US007520920B1

(12) United States Patent
Gregory et al.

(10) Patent No.: US 7,520,920 B1
(45) Date of Patent: Apr. 21, 2009

(54) GUARD COLUMNS FOR GAS CHROMATOGRAPHS AND GAS CHROMATOGRAPH-MASS SPECTROMETERS

(75) Inventors: Mark A. Gregory, Lafayette, IN (US); Garth E. Patterson, Brookston, IN (US); Anthony J. Cochran, Lafayette, IN (US); Jason L. Springston, Carmel, IN (US)

(73) Assignee: Griffin Analytical Technologies, West Lafayette, IN (US)

( * ) Notice: Subject to any disclaimer, the term of this patent is extended or adjusted under 35 U.S.C. 154(b) by 231 days.

(21) Appl. No.: 11/367,334

(22) Filed: Mar. 6, 2006

Related U.S. Application Data (60) Provisional application No. 60/658,149, filed on Mar. 4, 2005.

(51) Int. Cl.
*B01D 53/02* (2006.01)
(52) U.S. Cl. .............................. 96/106; 96/102; 96/105; 95/87; 73/23.35
(58) Field of Classification Search .................. 95/82, 95/87, 89; 96/101, 102, 105, 106; 73/23.35, 73/23.36, 23.37, 23.41, 23.42
See application file for complete search history.

(56) References Cited

U.S. PATENT DOCUMENTS

| | | | | |
|---|---|---|---|---|
| 4,383,839 A * | 5/1983 | Sisti et al. ...................... | 95/83 |
| 5,227,059 A * | 7/1993 | Shepherd ................... | 210/198.2 |
| 5,611,846 A | 3/1997 | Overton et al. | |
| 5,767,387 A * | 6/1998 | Wang ......................... | 73/23.42 |
| 6,095,572 A * | 8/2000 | Ford et al. ................... | 285/361 |
| 6,103,112 A * | 8/2000 | Sutton et al. .............. | 210/198.2 |
| 6,209,386 B1 | 4/2001 | Mustacich et al. | |
| 6,217,829 B1 | 4/2001 | Mustacich et al. | |
| 6,223,584 B1 | 5/2001 | Mustacich et al. | |
| 6,361,687 B1 * | 3/2002 | Ford et al. ............... | 210/198.2 |
| 6,490,852 B1 | 12/2002 | Mustacich et al. | |
| 6,530,260 B1 | 3/2003 | Mustacich et al. | |
| 6,652,625 B1 * | 11/2003 | Tipler et al. ..................... | 95/82 |
| 6,682,699 B2 | 1/2004 | Mustacich et al. | |
| 7,361,208 B2 * | 4/2008 | Botelho et al. ................. | 95/87 |

* cited by examiner

*Primary Examiner*—Duane S Smith
*Assistant Examiner*—Robert A Clemente
(74) *Attorney, Agent, or Firm*—Finnegan, Henderson, Farabow, Garrett & Dunner, LLP (57) ABSTRACT

The present invention discloses a gas chromatograph assembly. In one implementation, the assembly includes a sample injector and a guard column assembly. The guard column assembly includes a guard column connected to and downstream of the sample injector; a jacket with low thermal mass surrounding the guard column; a temperature controlled heater connected to the jacket to control the temperature of the jacket and thereby the temperature of the guard column; and an insulating housing surrounding the jacket. An analytical column is connected to and downstream of the guard column.

51 Claims, 12 Drawing Sheets

GUARD COLUMNS FOR GAS CHROMATOGRAPHS AND GAS CHROMATOGRAPH-MASS SPECTROMETERS

CROSS-REFERENCE TO RELATED APPLICATION

This application claims the benefit of U.S. Provisional Application No. 60/658,149, filed Mar. 4, 2005, by Mark Gregory and Garth Patterson, and titled GUARD COLUMNS FOR GAS CHROMATOGRAPHS AND GAS CHROMATOGRAPH-MASS SPECTROMETERS, the disclosure of which is expressly incorporated herein by reference.

FIELD OF THE INVENTION

The present invention relates to guard columns for gas chromatographs and gas chromatograph-mass spectrometers.

BACKGROUND OF THE INVENTION

Currently, gas chromatography is widely used for separation, identification, and determination of the chemical components of a mixture. Mass spectrometry (MS) is also widely used to qualify and quantify the composition, the structure, and isotopic ratios of various chemical samples. Frequently, it is valuable to use gas chromatography to separate the chemical components of a mixture and then use mass spectrometry to detect and analyze those chemical components. The benefits of combining these two techniques has lead to the creation of gas chromatograph-mass spectrometer instruments. In the standard setup of these instruments, the sample is introduced to the gas chromatograph first, where it is separated in the gas chromatograph analytical column. Following separation, the components are transported from the analytical column to the mass spectrometer for analysis.

Historically, gas chromatograph-mass spectrometers have been large instruments with substantial power requirements. Due to these size and power requirements, gas chromatograph-mass spectrometers have typically been limited to the laboratory. Presently, however, there is an increasing demand for portable gas chromatograph-mass spectrometers that can be used both in and out of the laboratory. Recently, the development of low thermal mass gas chromatographs and miniature mass analyzers has made portable gas chromatograph-mass spectrometers possible.

One common problem associated with gas chromatograph-mass spectrometers is that samples introduced into a gas chromatograph-mass spectrometer may contain chemical impurities at concentration levels many times that of the analytes of interest within the samples. When the samples are introduced into the analytical column of the gas chromatograph-mass spectrometer, these impurities tend to collect at the beginning of the analytical column. Over time, as the level of impurities on the column increases, the performance of the gas chromatograph-mass spectrometers diminishes.

Historically, the only remedy for this problem was to cut off sections of the analytical column as part of periodic maintenance. For large gas chromatograph-mass spectrometers, removal of sections of the analytical column may be a viable option. For newer portable gas chromatograph-mass spectrometers, however, this option is less viable because the analytical column is smaller and usually integrated into the overall assembly in such a way that sections cannot be removed.

More recently, guard columns have been used as an alternative remedy to the contamination problem. Guard columns are short inert columns or small diameter, e.g. capillary, tubings placed at the beginning of the analytical column. When guard columns are used, the impurities will instead be deposited in the guard column as opposed to the analytical column. Guard columns are designed to be relatively inexpensive and easily replaceable, such that when the guard columns become overly contaminated or fouled, they can then be quickly removed and replaced.

Because the guard column is connected to the analytical column, it is important to be able to control the temperature of the guard column so as not to adversely affect the transport of the volatilized sample. In the case of portable gas chromatograph-mass spectrometers, this temperature control must also be achievable without significantly increasing the size or power consumption of the instrument. In addition, the method of temperature control cannot affect the ease of replacing the guard column after it becomes overly contaminated. Present guard columns have not provided such temperature control within these limitations. Therefore, there is a need for a guard column for gas chromatograph-mass spectrometers that meets all these requirements.

SUMMARY OF THE INVENTION

Apparatus consistent with one embodiment of the invention provide a gas chromatograph assembly. The gas chromatograph assembly includes a sample injector and a guard column assembly. The guard column assembly includes a guard column connected to and downstream of the sample injector, a jacket with low thermal mass surrounding the guard column; a temperature controlled heater connected to the jacket to control the temperature of the jacket and thereby the temperature of the guard column; and an insulating housing surrounding the jacket. The gas chromatograph assembly also includes an analytical column connected to and downstream of the guard column.

Apparatus consistent with another embodiment of the invention provide a gas chromatograph assembly including a sample injector and a guard column assembly. The guard column assembly includes a replaceable guard column connected to and downstream of the sample injector; a first fitting connecting the sample injector to the guard column; a second fitting connecting the guard column to the analytical column; a jacket with low thermal mass surrounding the guard column, a temperature controlled heater connected to the jacket to control the temperature of the jacket and thereby the temperature of the guard column, wherein the jacket abuts the first and second fittings such that the temperature controlled heater also controls the temperature of the first and second fittings; and an insulating housing surrounding the jacket. The gas chromatograph assembly also includes an analytical column connected to and downstream of the guard column.

Apparatus consistent with another embodiment of the invention provide a gas chromatograph assembly comprising a sample injector and a first guard column assembly. The first guard column assembly includes a first guard column connected to and downstream of the sample injector, the first guard column having a low thermal mass; a first jacket with low thermal mass surrounding the first guard column; a first temperature controlled heater connected to the first jacket to control the temperature of the first jacket and thereby the temperature of the first guard column; and a first insulating housing surrounding the first jacket. The gas chromatograph assembly also includes an analytical column connected to and downstream of the guard column and a second guard column assembly. The second guard column assembly includes a second guard column connected to and downstream of the analytical column, the second guard column having a low thermal mass; a second jacket with low thermal mass surrounding the second guard column; a second temperature controlled heater connected to the second jacket to control the temperature of the second jacket and thereby the temperature of the second guard column; and a second insulating housing surrounding the second jacket. Additionally, the gas chromatograph assembly includes an outlet connected to and downstream of the second guard column.

Apparatus consistent with another embodiment of the invention provide a replaceable guard column assembly for a gas chromatograph assembly having a sample injector for introducing a sample into the gas chromatograph assembly and an analytical column for analyzing the sample. The guard column assembly includes a replaceable guard column connected to and downstream of the sample injector and connected to and upstream of the analytical column; a jacket with low thermal mass surrounding the guard column; a temperature controlled heater connected to the jacket to control the temperature of the jacket and thereby the temperature of the guard column; and an insulating housing surrounding the jacket.

Apparatus consistent with another embodiment of the invention provide a gas chromatograph assembly including means for injecting a sample; means for removing impurities from the injected sample; means for controlling the temperature of the impurity removing means; and means for separating chemical components of the injected sample.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

DESCRIPTION OF THE EMBODIMENTS

Reference will now be made in detail to the present embodiment of the invention, an example of which is illustrated in the accompanying drawings. Wherever possible, the same reference numbers will be used throughout the drawings to refer to the same or like parts.

Figure 1:
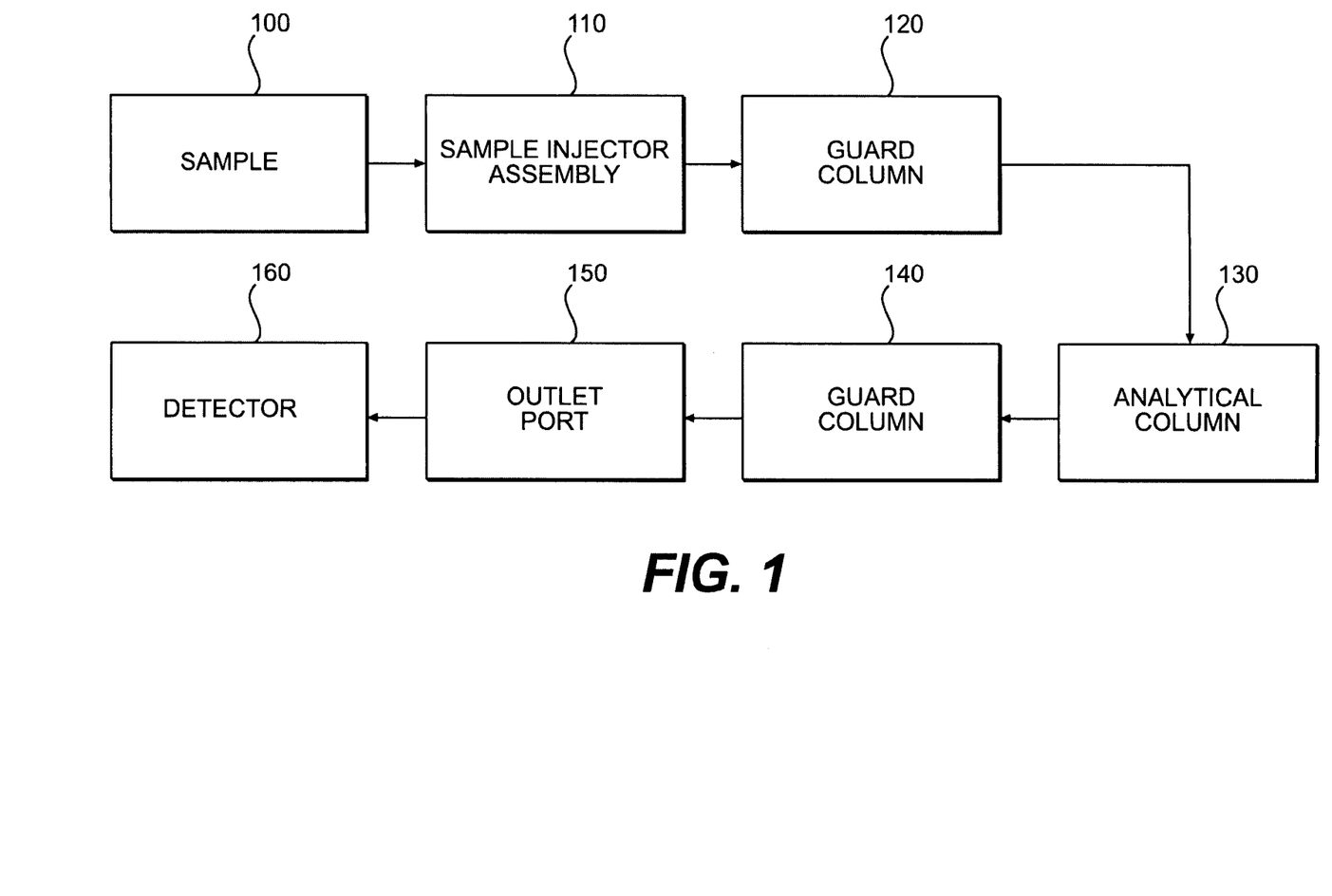
FIG. 1 is a flow diagram of sample flow path in a gas chromatograph assembly consistent with one embodiment of the invention.

FIG. 1 is a flow diagram of sample flow path in a gas chromatograph assembly consistent with one embodiment of the invention. As shown in FIG. 1, in one implementation, the flow path of a sample 100 introduced into a gas chromatograph assembly consistent with one embodiment of the invention is as follows: sample 100 is introduced into a sample injector assembly 110 where it is flash vaporized; the sample then travels through a guard column 120 into an analytical column 130; in analytical column 130, the chemical components of the sample are separated; the separated chemical components then travel through a second guard column 140 to an outlet port 150; from outlet port 150, the separated chemical components are sent to a detector 160, such as a mass spectrometer, for analysis. Each of these elements is described in detail below. This implementation is merely exemplary, and other implementations and flow paths may also be used.

FIGS. 2-8 illustrate several views of a gas chromatograph assembly 200 having the sample flow path illustrated in FIG. 1 consistent with one embodiment of the invention. It should be understood that gas chromatograph assembly 200 depicted could be a stand-alone gas chromatograph assembly or the gas chromatograph component of a gas chromatograph-mass spectrometer assembly. In addition, gas chromatograph assembly 200 depicted is portable, however, the invention has application in both portable and non-portable gas chromatograph assemblies.

As indicated above, the sample is introduced into gas chromatograph assembly 200 through sample injector assembly 212. Sample injector assembly 212 includes a sample injector 210, which is a port for injecting the sample to be analyzed. Sample injectors are well known in the art, and any suitable sample injector may be used. Sample injector assembly 212 includes a carrier gas inlet 215. Carrier gas inlet 215 is a port for allowing a carrier gas to be introduced into the gas chromatograph assembly. The carrier gas is introduced at a sufficient pressure to force the sample through gas chromatograph assembly 200 for analysis. The carrier gas may be any suitable chemically inert gas, such as nitrogen, helium, argon, or carbon dioxide.

Sample injector assembly 212 also includes a split vent 225. The purpose of split vent 225 is to control the sample size that is analyzed by the system. After introduction of the carrier gas, it may desirable to allow only a portion of the sample to proceed on to analytical column 240. If split vent 225 is opened some of the carrier gas will exit split vent 225 causing a portion of the sample to exit split vent 225. Therefore, by opening split vent 225 to varying degrees, the amount of sample that enters analytical column 240 can be controlled. Split vent 225 may be constructed as is well known in the art. This implementation is merely exemplary, and other methods of controlling the amount of the sample entering analytical column 240 may be used.

Sample injector assembly 212 also includes a septum purge outlet 217. Septum purge outlet 217 prevents septum bleed components from entering analytical column 240. Septum purge outlet 217 may be constructed as is well known in the art.

In this implementation, sample injector assembly 212 also includes a heater 260. Heater 260 raises the temperature of the entire sample injector assembly 212, such that vaporization of the sample occurs immediately upon injection into sample injector assembly 212. Heater 260 may be any suitable heating device sufficient to vaporize the sample as is commonly used in gas chromatograph assemblies. In one implementation, the heater is a cartridge heater. This implementation is merely exemplary, and other heaters may also be used.

From the sample injector assembly 212, the vaporized sample next passes into guard column 285. Guard column 285 filters any low volatility components or particulate matter from the introduced samples that may be present prior to introduction of the sample to analytical column 240. In one implementation, guard column 285 is constructed such that it has a low thermal mass. By having a low thermal mass, the temperature of the guard column can be quickly and easily controlled with low power requirements as will be described herewith. For example, in one implementation, the guard column will be constructed of activated or deactivated fused silica or stainless steel capillary column, cut to an appropriate length and having an inner diameter comparable to that of the analytical column, i.e. approximately 0.10-0.25 mm. These implementations are merely exemplary, and other implementations resulting in low thermal mass may also be used.

Figure 7:
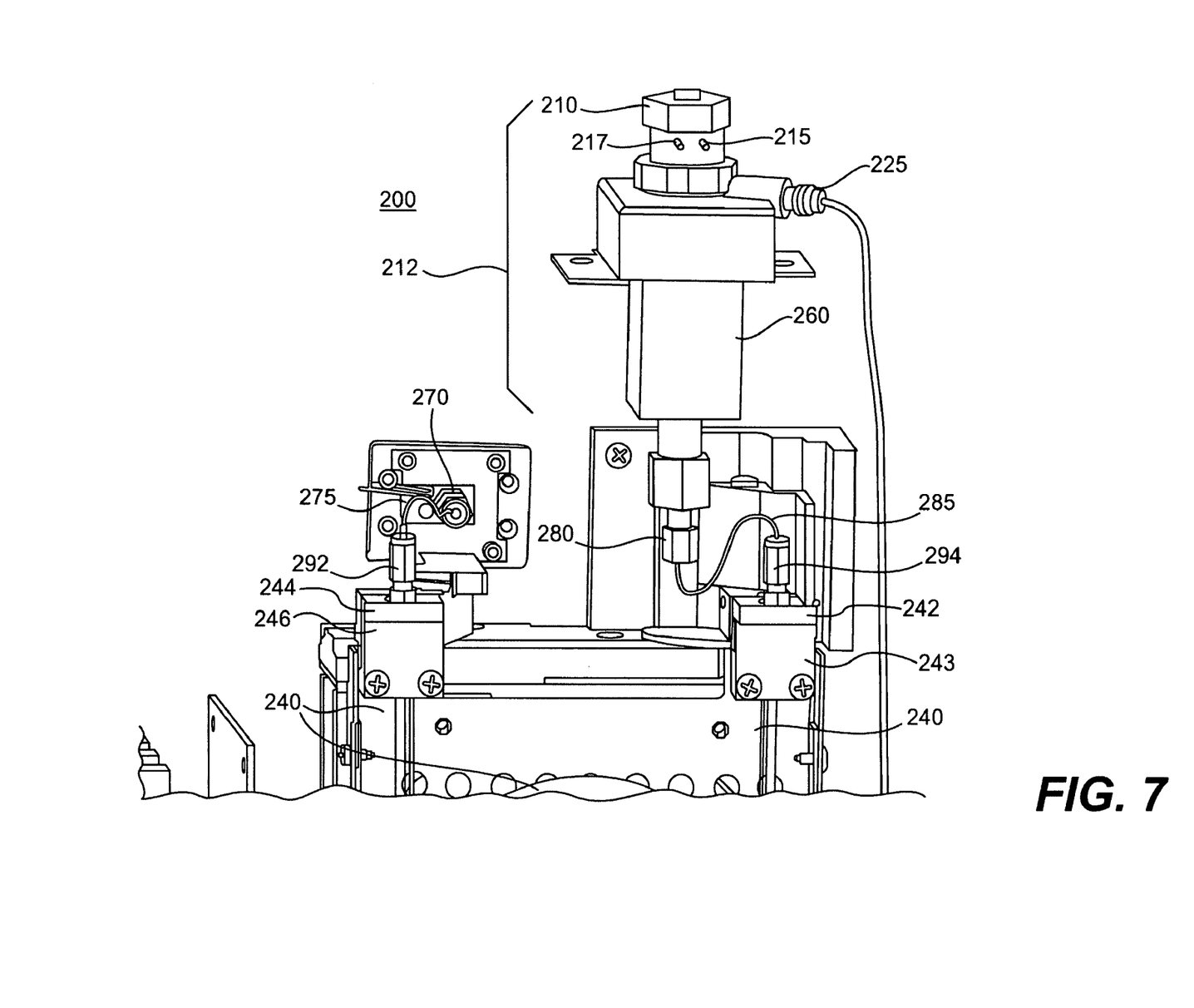
FIG. 7 is a partial front perspective view of a gas chromatograph assembly with the insulating housings and jackets partially removed consistent with one embodiment of the invention.
Figure 8:
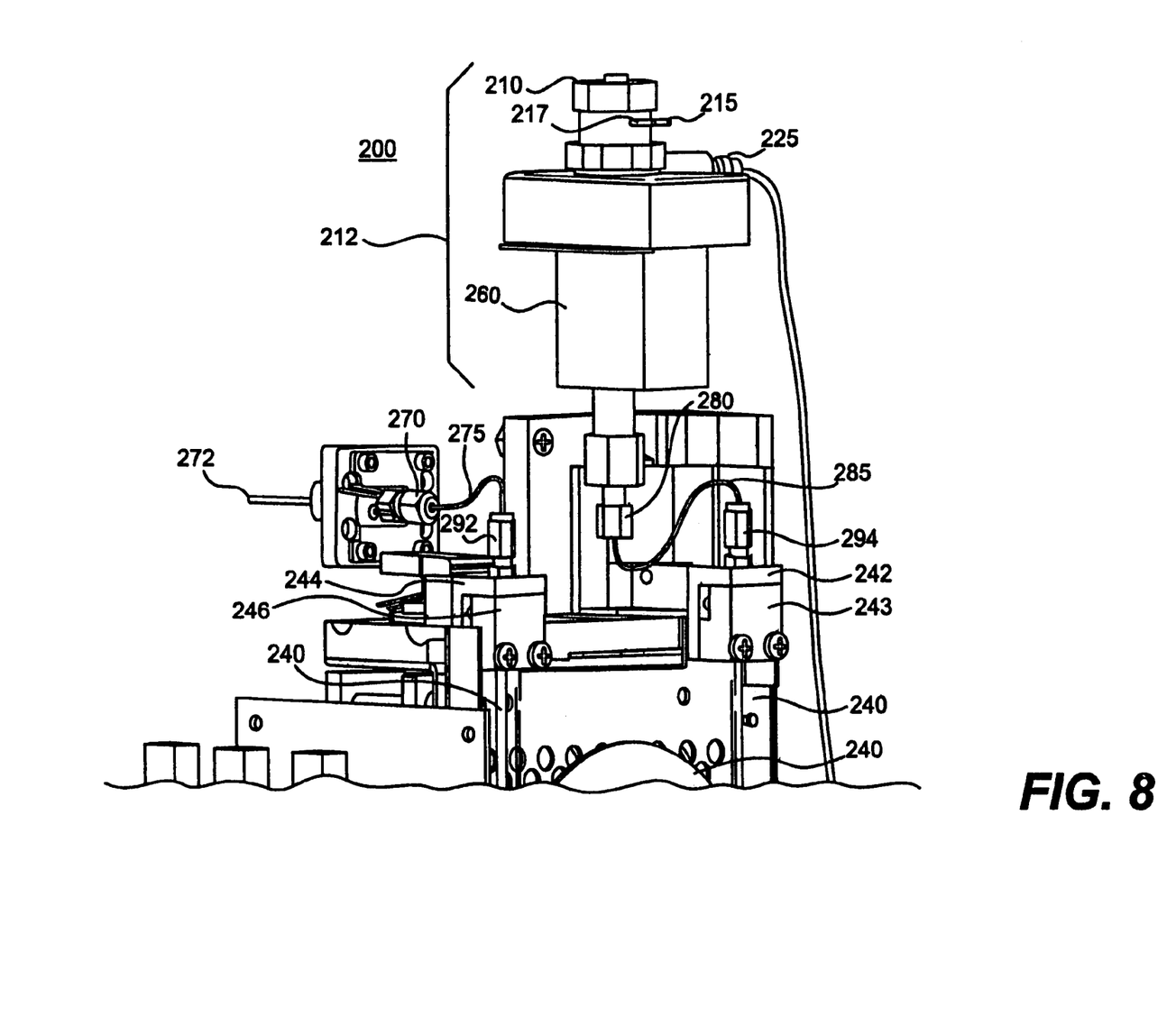
FIG. 8 is another partial side perspective view of a gas chromatograph assembly with the insulating housings and jackets partially removed consistent with one embodiment of the invention.
Figure 9A:
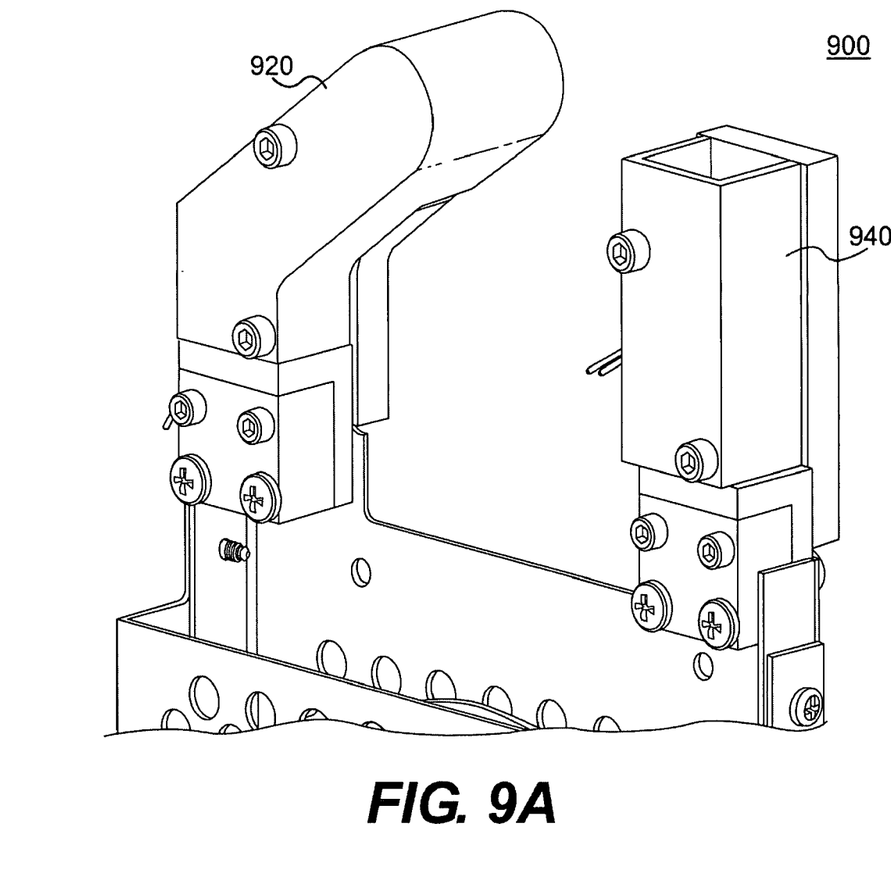
FIG. 9A is a partial front perspective view of a gas chromatograph assembly with jackets consistent with another embodiment of the invention.
Figure 9B:
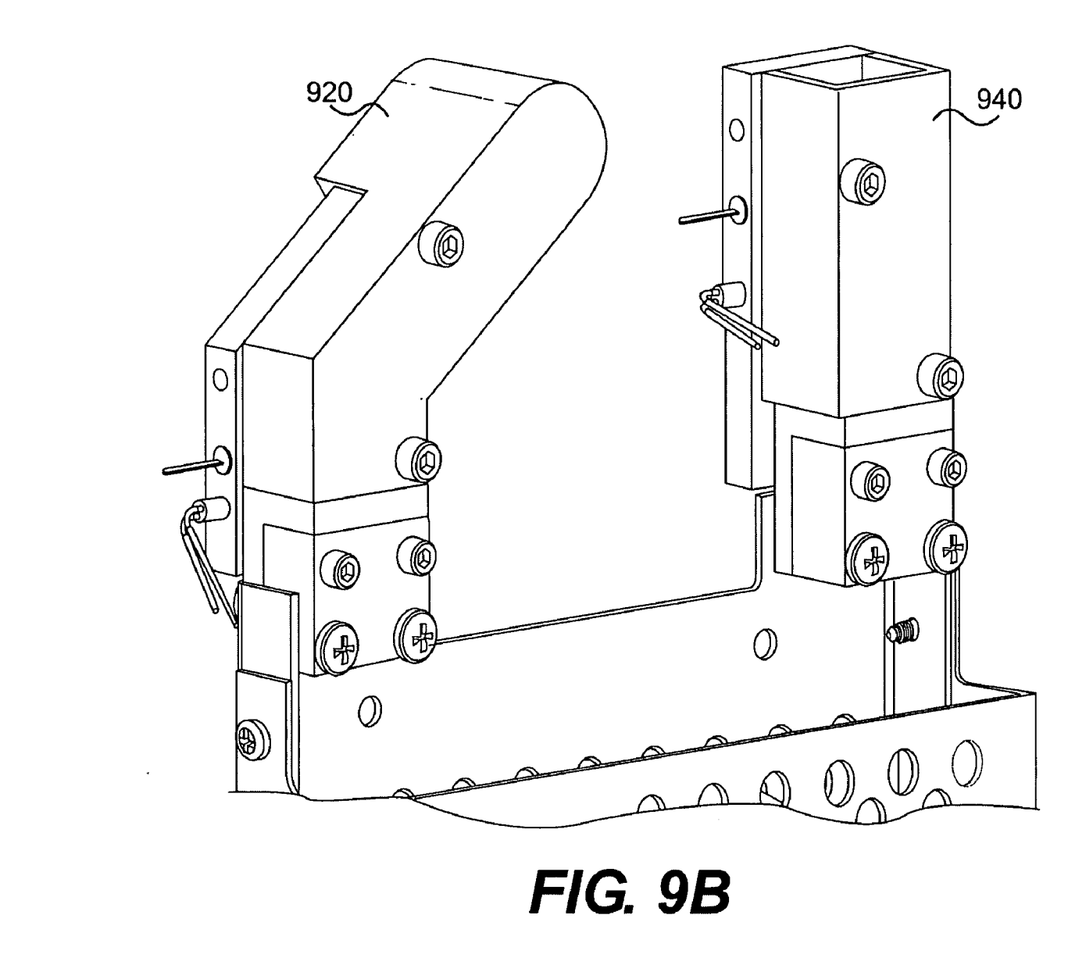
FIG. 9B is a partial front perspective view of a gas chromatograph assembly with jackets consistent with another embodiment of the invention, as shown in FIG. 9A.
Figure 10A:
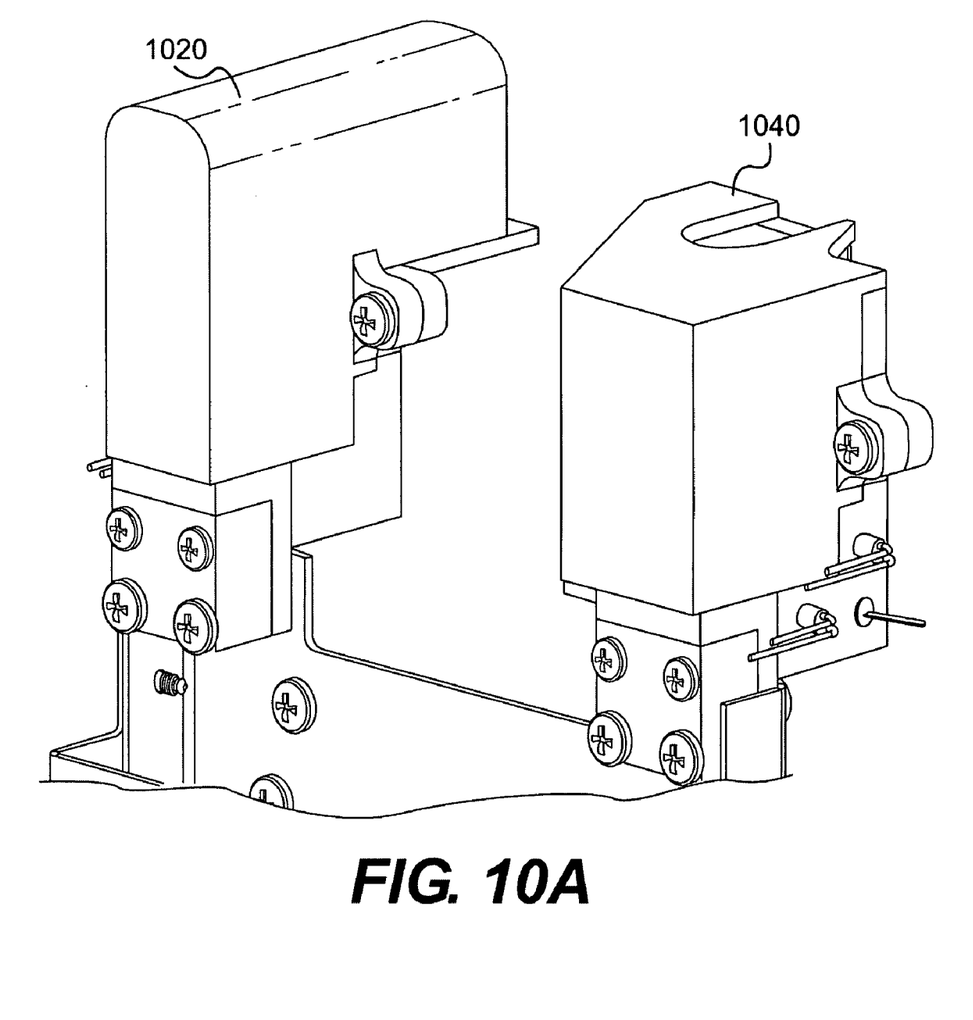
FIG. 10A is a partial front perspective view of a gas chromatograph assembly with jackets consistent with another embodiment of the invention.
Figure 10B:
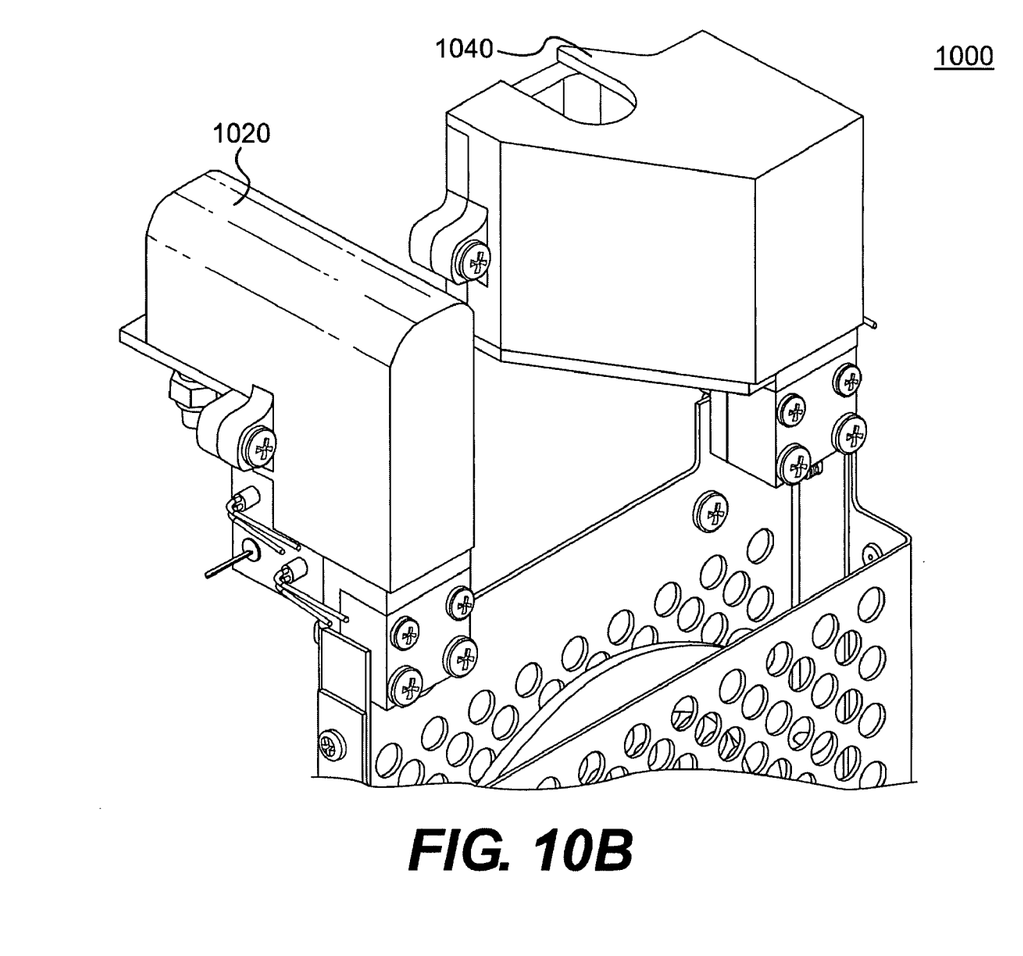
FIG. 10B is a partial front perspective view of a gas chromatograph assembly with jackets consistent with another embodiment of the invention, as shown in FIG. 10B.

As shown in FIGS. 7-8, guard column 285 is attached to sample injector assembly 212 and analytical column 240 via fittings 280 and 294, respectively. In one implementation, fittings 280 and 294 are zero dead volume fittings and polyimide ferrules such as those available from SGE Incorporated of Austin, Tex. In another implementation, graphite ferrules are used. The use of fittings allows for guard column 285 to be easily detached from sample injector assembly 212 and analytical column 240 and replaced when necessary. This implementation is merely exemplary, and other implementations may also be used.

Figure 5:
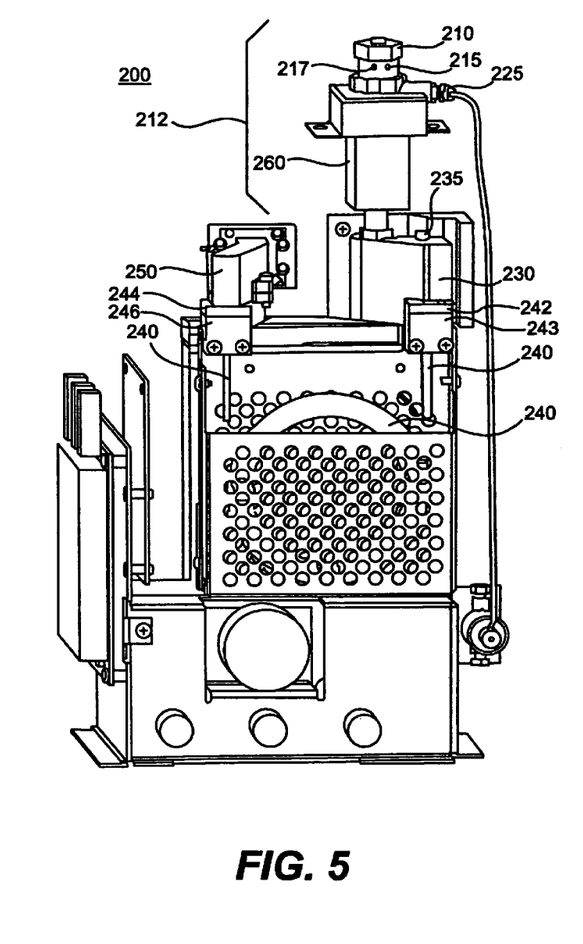
FIG. 5 is a front perspective view of a gas chromatograph assembly with insulating housings partially removed consistent with one embodiment of the invention.
Figure 6:
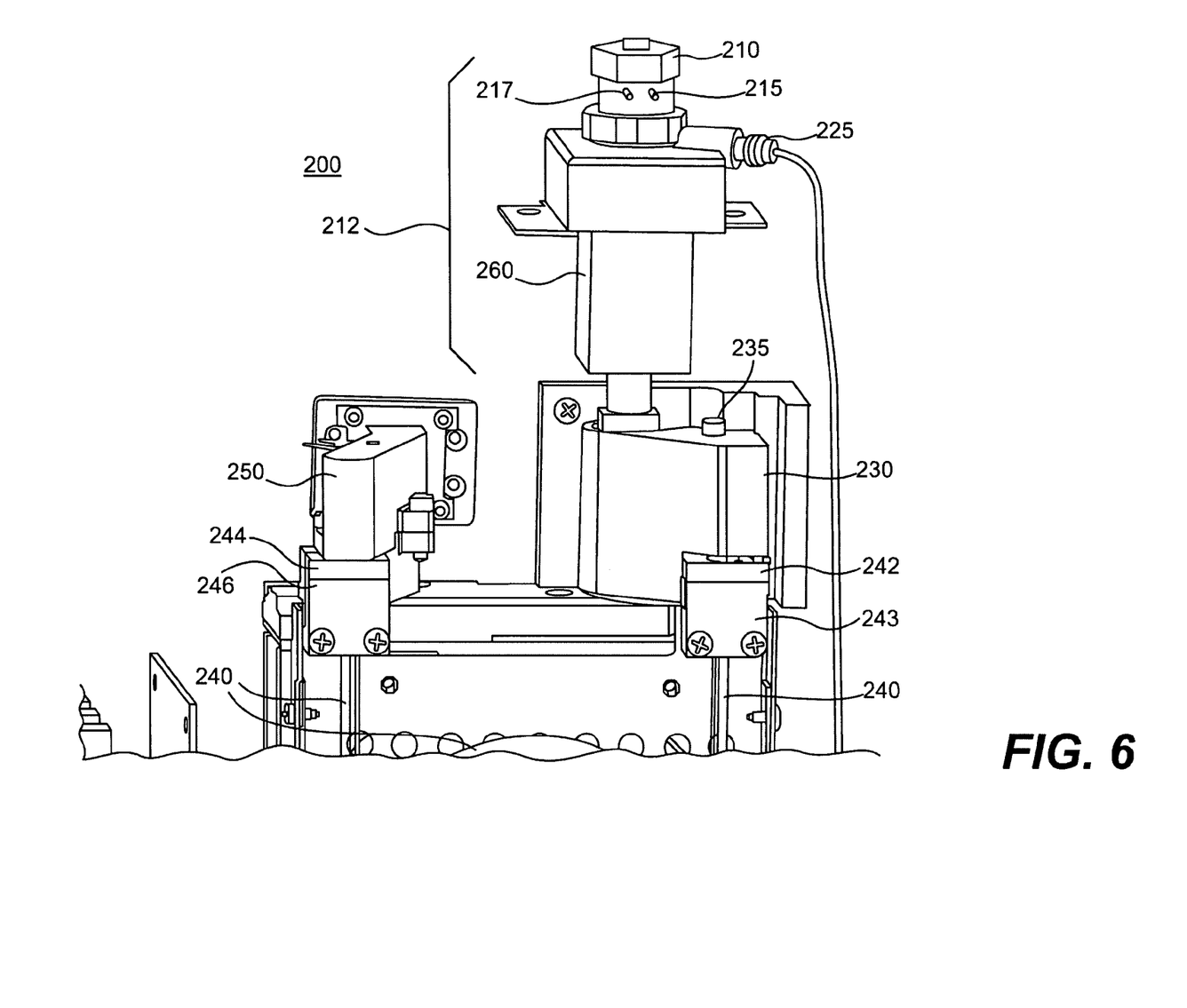
FIG. 6 is a partial front perspective view of a gas chromatograph assembly with insulating housings partially removed consistent with one embodiment of the invention.

Temperature control of guard column 285 is important to maintain the sample temperature and avoid affecting the analysis of the sample. In this implementation, the temperature of guard column 285 is controlled by heating an air bath surrounding the guard column. The air bath is created by the heating of the air inside a jacket 230 surrounding guard column 285 (shown in FIGS. 5-6). In one implementation, as shown in FIGS. 5-6, jacket 230 is a two-piece aluminum alloy jacket that runs from the bottom of the heater to the head of analytical column 240, thus enclosing fittings 280 and 294 and guard column 285. In this implementation, the two pieces are held together by means of a thumbscrew 235. This construction allows for jacket 230 to be easily removed so that guard column 285 can be accessed and replaced as necessary without the need for additional tools. In addition, the low thermal mass of the aluminum jackets allows for less power consumption upon heating, takes less time to heat up, and takes less time to cool down. In one implementation, an aluminum alloy which has high thermal conductivity is used for the two part heating jacket 230, so that it will transmit heat well, have relatively high strength so as not to become misshaped, have good workability which means it can easily be cast or machined, and have a high resistance to deterioration caused by oxidation or chemical action. In one implementation, the mass of the aluminum jacket will be 0.175 lb. In another implementation, the mass of the aluminum jacket will be 0.346 lb. It should be understood that jacket 230 may be constructed of low thermal mass materials other than aluminum. This implementation is merely exemplary, and other implementations may also be used.

The air inside jacket 230 is heated by raising the temperature of jacket 230. The heated air will, in turn, heat guard column 285. The temperature of jacket 230 may be controlled using any suitable method. In one implementation, the temperature will be controlled with a Resistance Temperature Detector (RTD) temperature controller and a nickel-chromium heater. For example, in one implementation, a 100 ohm platinum RTD element for measurement and a 30-watt nickel-chromium heater may be used. This implementation is merely exemplary, and other implementations may also be used.

In one implementation, jacket 230 abuts fittings 280 and 294 such that the temperature of jacket 230 will also heat fittings 280 and 294 via conduction. In another implementation, jacket 230 completely surrounds fitting 280 so that fitting 280 is also heated by the heated air inside jacket 230. In this implementation, jacket 230 partially surrounds fitting 294, which is attached to a bracket 242. A fitting jacket 243 surrounds the portion of fitting 294 outside of jacket 230. In this implementation, fitting 294 is in physical contact with bracket 242. As the temperature of jacket 230 is raised, the temperature of bracket 242 is also raised, thereby heating fitting 294. The temperature of the air inside fitting jacket 243 is also raised further serving to heat fitting 294. These implementations are merely exemplary, and other implementations may also be used.

In one implementation, the temperature of guard column 285 is controlled and regulated independent of analytical column 240. Maintaining constant temperature saves time and power consumption because the temperature of guard column 285 does not have to be continuously cycled. Furthermore, the temperature can be adjusted to optimize the sample analysis by the user.

Figure 2:
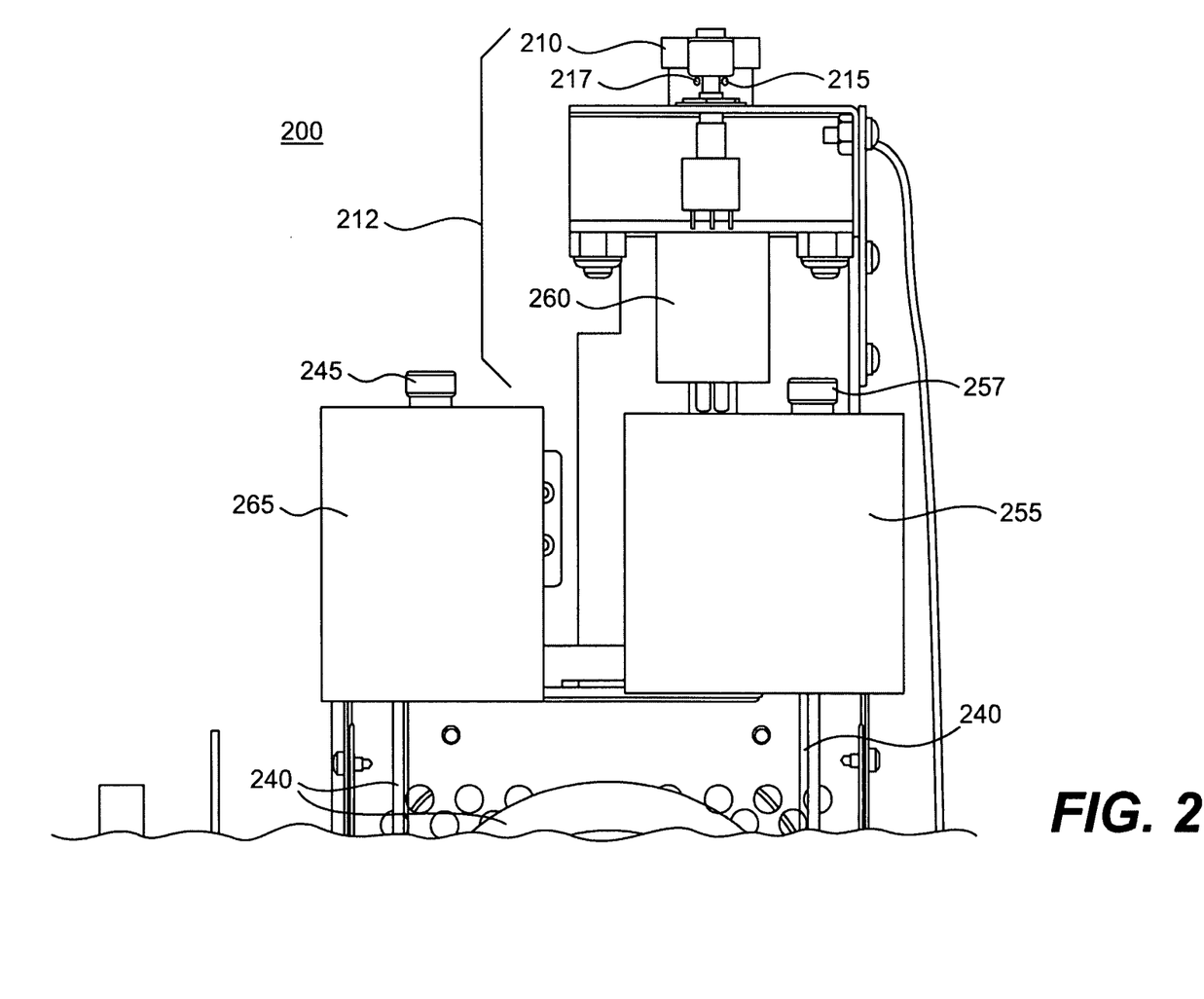
FIG. 2 is a partial front view of a gas chromatograph assembly consistent with one embodiment of the invention.
Figure 3:
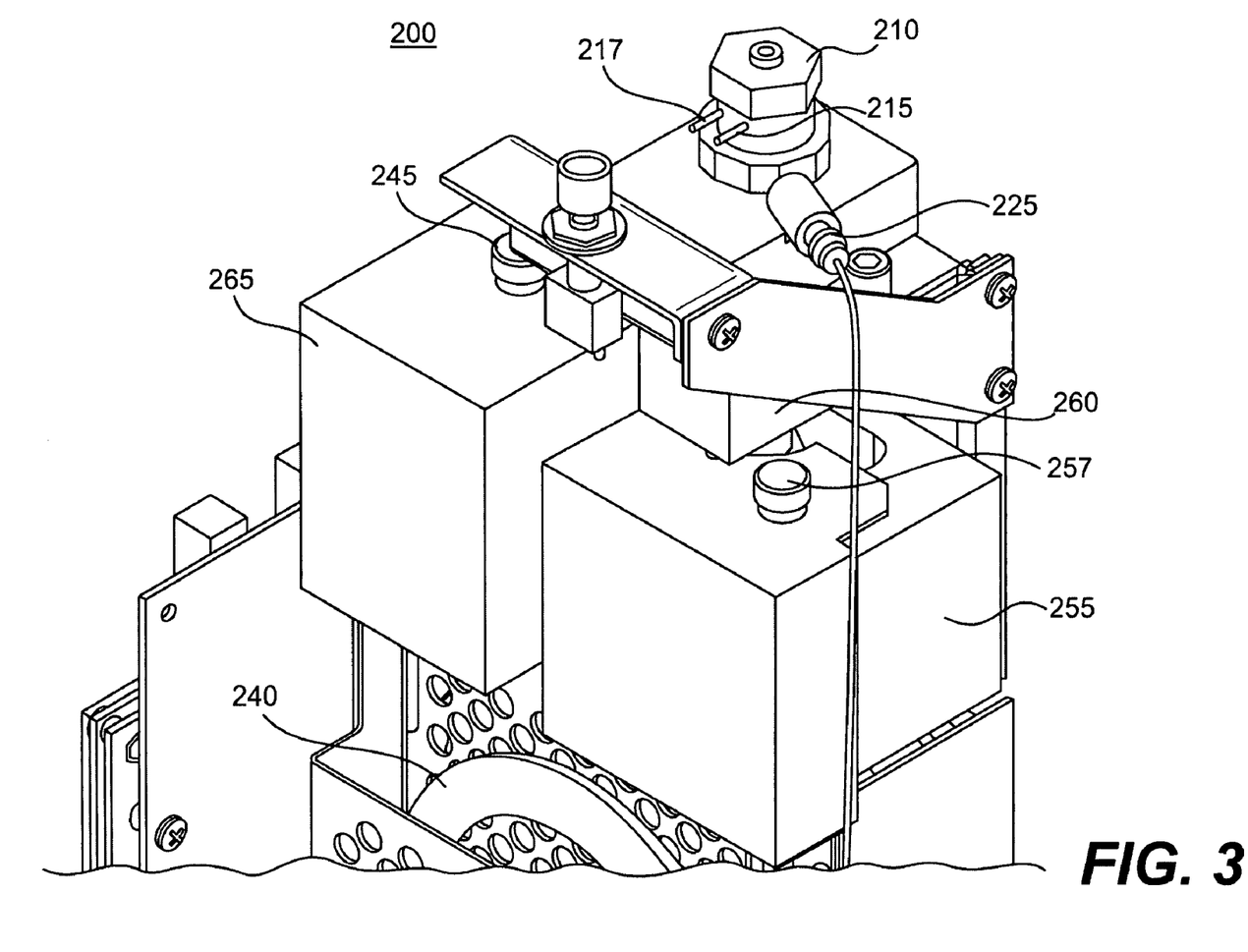
FIG. 3 is a partial top perspective view of a gas chromatograph assembly consistent with one embodiment of the invention.
Figure 4:
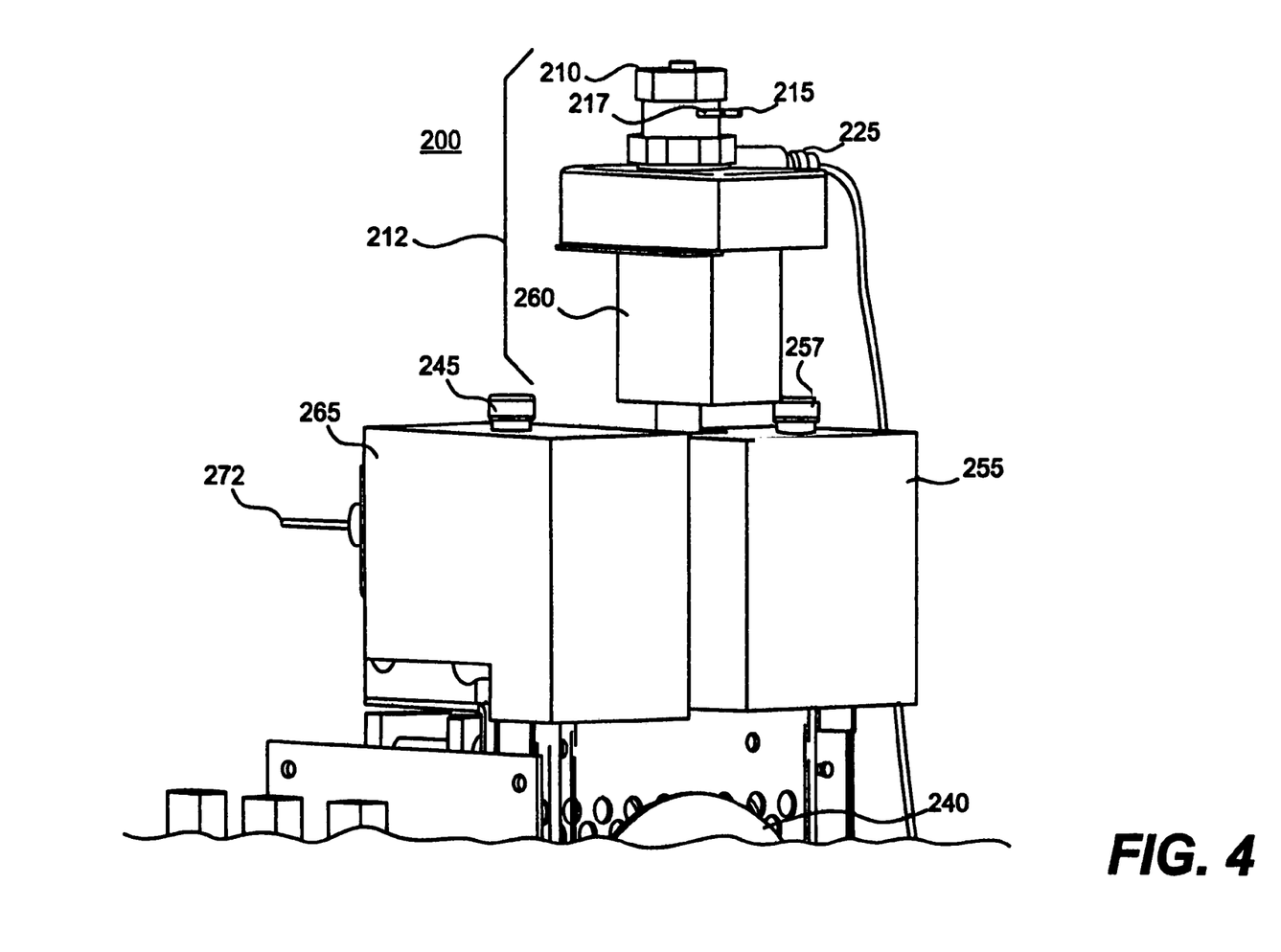
FIG. 4 is a partial side perspective view of a gas chromatograph assembly consistent with one embodiment of the invention.

As shown in FIGS. 2-4, in this implementation, jacket 230 is encapsulated by an insulated housing 255. Insulating jacket 230 helps maintain constant temperatures, which reduces power consumption and eliminates cold spots in guard column 285 which could lead to adsorption of sample components and hinder the amount of sample and time taken to reach the outlet. In this implementation, housing 255 is a two-piece housing held together by means of a thumbscrew 257. This construction also allows for housing 255 to be easily removed so that guard column 285 can be accessed. In one implementation, insulated housing 255 is constructed with machined Zircal-18 or Zircal-45 available from BNZ Materials Inc. of Littleton, Colo. Zircal-18 and Zircal-45 are non-asbestos high temperature calcium silicate refractory materials that have resistance to thermal shock which means that as the temperature of the system is continuously increased and decreased the material will not degrade over time. Zircal-18 and Zircal-45 also have low thermal conductivity so as not to transmit heat, high structural strength at elevated temperatures which means that they will not become brittle and will maintain their integrity, incombustibility so as not to be flammable at high temperatures, and are easily machined to conform their shape to fit different applications. In another implementation, insulated housing 255 is a two-piece housing in which one piece is constructed of machined Zircal-18 or Zircal-45 and the other piece is fiber board. This implementation is merely exemplary, and other implementations and materials may also be used.

As shown in FIGS. 7-8, guard column 285 is attached to the inlet of analytical column 240 by means of fitting 294. Analytical column 240 is any analytical column such as those typically used in gas chromatograph assemblies. As is well understood in the art, after passing through analytical column 240, the sample will be separated into its components. From analytical column 240, the sample may then be sent to an outlet 272. From outlet 272, the sample may then be sent to any number of detectors. In particular, in one implementation, the sample will be sent to a mass spectrometer for analysis. This implementation is merely exemplary, and other implementations may also be used.

As shown in FIGS. 7-8, a guard column 275 may also be included between the analytical column 240 and gas chromatograph outlet 272. As shown in the figures, in one implementation, guard column 275 is of the same construction as guard column 285 and includes a jacket 250 closed by a thumbscrew (not shown) and insulated housing 265 closed by thumbscrew 245. In addition, the temperature of guard column 285 will be controlled in the same way as guard column 285 at the inlet port. In one implementation, a bracket 244 and fitting jacket 246 is also included around fitting 292.

It should be understood that the disclosed construction provides a replaceable "head" and "tail" at the inlet and outlet, respectively. of analytical column 240, which is important as the head is the most likely to become fouled with large concentration chemical impurities and particulates, and the head and tail are the most likely to experience physical damage during instrument handling. It is time-consuming and costly to replace the low thermal mass analytical column, due to its integration into the heating and temperature sensing assembly. A purpose of guard columns 285 and 275 is to help prolong the life of analytical column 240 by providing a replaceable head and tail at the inlet and outlet, respectively of analytical column 240, as the ends of analytical column 240 are the most likely to be damaged. It is therefore advantageous to have the low thermal mass guard column be easily accessible and changeable for the user.

In this regard, each guard columns 285 and 275 is housed separately with its own insulated, heated jacket 230, 250. The insulating housings 255, 265 are easily removable as are the tops of the two-piece jackets 230, 250. These two components house the entire heated guard columns 285 and 275 and fittings 270, 280, 292, 294.

In order to replace guard column 285, a user would unscrew thumbscrew 257 and remove insulating housing 255 to reveal jacket 230. Next, the user would unscrew thumbscrew 235 and remove jacket 230 to reveal fittings 280 and 294 and guard column 285. The user would then undo fittings 280 and 294 to release guard column 285. Guard column 285 would be replaced with a new guard column, which would be attached to system by fittings 280 and 294 or new fittings if the user so desired. Next, jacket 230 would again be placed around the new guard column and attached with thumbscrew 235. Finally, housing 255 would be placed around jacket 230 and secured with thumbscrew 257. The same steps may be taken to replace guard column 275 as well.

It should be understood that FIGS. 1-8 show one possible construction of jackets and insulating housing for heating a guard column consistent with one embodiment of the invention. This construction is only exemplary and the jacket and housings may be constructed in other suitable shapes and sizes. FIGS. 9A and 9B and FIGS. 10A and 10B show two additional constructions for jackets consistent with the invention. In the embodiment show in FIGS. 9A and 9B, gas chromatograph assembly 900 includes jackets 920 and 940 designed to fit around guard columns at the "head" and "tail" of the assembly. As shown, jackets 920 and 940 may be removed by undoing fasteners. Similarly, in the embodiment show in FIGS. 10A and 10B, gas chromatograph assembly 1000 includes jackets 1020 and 1040 designed to fit around guard columns at the "head" and "tail" of the assembly. As shown, jackets 1020 and 1040 may also be removed by undoing fasteners.

As described above, therefore, other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents. In this context, equivalents mean each and every implementation for carrying out the functions recited in the claims, even if not explicitly described therein.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A gas chromatograph assembly comprising:
   a sample injector;
   a guard column assembly including:
      a guard column connected to and downstream of the sample injector;
      a jacket with low thermal mass surrounding the guard column;
      a temperature controlled heater connected to the jacket to control the temperature of the jacket and thereby the temperature of the guard column; and
      an insulating housing surrounding the jacket; and
   an analytical column connected to and downstream of the guard column.

2. The gas chromatograph assembly of claim 1, wherein the guard column is replaceable.

3. The gas chromatograph assembly of claim 1, further comprising:
   a first fitting connecting the sample injector to the guard column; and
   a second fitting connecting the guard column to the analytical column; and
   wherein the jacket abuts the first and second fittings such that the temperature controlled heater also controls the temperature of the first and second fittings.

4. The gas chromatograph assembly of claim 3, wherein the jacket completely surrounds the first fitting and partially surrounds the second fitting and further comprising:
   a bracket abutting the second fitting; and a fitting jacket connected to the bracket and surrounding the portion of the second fitting not surrounded by the jacket.

5. The gas chromatograph assembly of claim 3, wherein the first and second fittings comprise a zero dead volume fitting.

6. The gas chromatograph assembly of claim 1, wherein the jacket is constructed of aluminum alloy.

7. The gas chromatograph assembly of claim 1, wherein the jacket is constructed of at least two separable pieces that allow access to the guard column when separated.

8. The gas chromatograph assembly of claim 1, wherein the temperature controlled heater is a nickel-chromium heater.

9. The gas chromatograph assembly of claim 1, further comprising a temperature detector in the jacket.

10. The gas chromatograph assembly of claim 9, wherein the temperature detector is a resistance temperature detector.

11. The gas chromatograph assembly of claim 1, wherein the insulating housing is constructed of a non-asbestos high temperature calcium silicate refractory material.

12. The gas chromatograph assembly of claim 1, wherein the insulating housing is constructed of at least two separable pieces that allow access to the jacket when separated.

13. The gas chromatograph assembly of claim 1, wherein the temperature of the guard column is controlled independently of the analytical column.

14. A gas chromatograph assembly comprising:
a sample injector;
a guard column assembly including:
a replaceable guard column connected to and downstream of the sample injector;
a first fitting connecting the sample injector to the guard column;
a second fitting connecting the guard column to the analytical column;
a jacket with low thermal mass surrounding the guard column,
a temperature controlled heater connected to the jacket to control the temperature of the jacket and thereby the temperature of the guard column, wherein the jacket abuts the first and second fittings such that the temperature controlled heater also controls the temperature of the first and second fittings; and
an insulating housing surrounding the jacket; and
an analytical column connected to and downstream of the guard column.

15. The gas chromatograph assembly of claim 14, wherein the first and second fittings comprise a zero dead volume fitting.

16. The gas chromatograph assembly of claim 14, wherein the jacket is constructed of aluminum alloy.

17. The gas chromatograph assembly of claim 14, wherein the jacket is constructed of at least two separable pieces that allow access to the guard column when separated.

18. The gas chromatograph assembly of claim 14, wherein the temperature controlled heater is a nickel-chromium heater.

19. The gas chromatograph assembly of claim 14, further comprising a temperature detector in the jacket.

20. The gas chromatograph assembly of claim 19, wherein the temperature detector is a resistance temperature detector.

21. The gas chromatograph assembly of claim 14, wherein the insulating housing is constructed of a non-asbestos high temperature calcium silicate refractory material.

22. The gas chromatograph assembly of claim 14, wherein the insulating housing is constructed of at least two separable pieces that allow access to the jacket when separated.

23. The gas chromatograph assembly of claim 14, wherein the temperature of the guard column is controlled independently of the analytical column.

24. The gas chromatograph assembly of claim 14, wherein the jacket completely surrounds the first fitting and partially surrounds the second fitting and further comprising:
a bracket abutting the second fitting; and
a fitting jacket connected to the bracket and surrounding the portion of the second fitting not surrounded by the jacket.

25. A gas chromatograph assembly comprising:
a sample injector;
a first guard column assembly including:
a first guard column connected to and downstream of the sample injector;
a first jacket with low thermal mass surrounding the first guard column;
a first temperature controlled heater connected to the first jacket to control the temperature of the first jacket and thereby the temperature of the first guard column; and
a first insulating housing surrounding the first jacket;
an analytical column connected to and downstream of the guard column;
a second guard column assembly including:
a second guard column connected to and downstream of the analytical column;
a second jacket with low thermal mass surrounding the second guard column;
a second temperature controlled heater connected to the second jacket to control the temperature of the second jacket and thereby the temperature of the second guard column; and
a second insulating housing surrounding the second jacket; and
an outlet connected to and downstream of the second guard column.

26. The gas chromatograph assembly of claim 25, wherein the first and second guard columns are replaceable.

27. The gas chromatograph assembly of claim 25, further comprising:
a first fitting connecting the sample injector to the first guard column;
a second fitting connecting the first guard column to the analytical column, wherein the first jacket abuts the first and second fittings such that the first temperature controlled heater also controls the temperature of the first and second fittings;
a third fitting connecting the analytical column to the second guard column; and
a fourth fitting connecting the second guard column to the outlet, wherein the second jacket abuts the third and fourth fittings such that the second temperature controlled heater also controls the temperature of the first and second fittings.

28. The gas chromatograph assembly of claim 27, wherein the first jacket completely surrounds the first fitting and partially surrounds the second fitting and wherein the second jacket completely surrounds the fourth fitting and partially surrounds the third fitting and further comprising:
a first bracket abutting the second fitting;
a first fitting, jacket connected to the bracket and surrounding the portion of the second fitting not surrounded by the first jacket;
a second bracket abutting the third fitting;

a second fitting jacket connected to the bracket and surrounding the portion of the third fitting not surrounded by the second jacket.

29. The gas chromatograph assembly of claim 25, wherein the first, second, third, and fourth fittings comprise a zero dead volume fitting.

30. The gas chromatograph assembly of claim 25, wherein the first and second jackets are constructed of aluminum alloy.

31. The gas chromatograph assembly of claim 25, wherein the first and second jackets are constructed of at least two separable pieces that allow access to the first and second guard columns when separated.

32. The gas chromatograph assembly of claim 25, wherein the first and second temperature controlled heaters are nickel-chromium heater.

33. The gas chromatograph assembly of claim 25, further comprising a first temperature detector in the first jacket and a second temperature detector in the second jacket.

34. The gas chromatograph assembly of claim 33, wherein the first and second temperature detectors are resistance temperature detectors.

35. The gas chromatograph assembly of claim 25, wherein the first and second insulating housings are constructed of a non-asbestos high temperature calcium silicate refractory material.

36. The gas chromatograph assembly of claim 25, wherein the first and second insulating housings are constructed of at least two separable pieces that allow access to the first and second jackets when separated.

37. The gas chromatograph assembly of claim 25, wherein the temperature of the first and second guard columns is controlled independently of the analytical column.

38. A replaceable guard column assembly for a gas chromatograph assembly having a sample injector for introducing a sample into the gas chromatograph assembly and an analytical column for analyzing the sample, the guard column assembly comprising:
 a replaceable guard column connected to and downstream of the sample injector and connected to and upstream of the analytical column;
 a jacket with low thermal mass surrounding the guard column;
 a temperature controlled heater connected to the jacket to control the temperature of the jacket and thereby the temperature of the guard column; and
 an insulating housing surrounding the jacket.

39. The replaceable guard column assembly of claim 38, further comprising:
 a first fitting connecting the sample injector to the guard column; and
 a second fitting connecting the guard column to the analytical column; and
 wherein the jacket abuts the first and second fittings such that the temperature controlled heater also controls the temperature of the first and second fittings.

40. The replaceable guard column assembly of claim 39, wherein the jacket completely surrounds the first fitting and partially surrounds the second fitting and further comprising:
 a bracket abutting the second fitting; and
 a fitting jacket connected to the bracket and surrounding the portion of the second fitting not surrounded by the jacket.

41. The replaceable guard column assembly of claim 38, wherein the first and second fittings comprise a zero dead volume fitting.

42. The replaceable guard column assembly of claim 38, wherein the jacket is constructed of aluminum alloy.

43. The replaceable guard column assembly of claim 38, wherein the jacket is constructed of at least two separable pieces that allow access to the guard column when separated.

44. The replaceable guard column assembly of claim 38, wherein the temperature controlled heater is a nickel-chromium heater.

45. The replaceable guard column assembly of claim 38, further comprising a temperature detector in the jacket.

46. The replaceable guard column assembly of claim 45, wherein the temperature detector is a resistance temperature detector.

47. The replaceable guard column assembly of claim 38, wherein the insulating housing is constructed of a non-asbestos high temperature calcium silicate refractory material.

48. The replaceable guard column assembly of claim 38, wherein the insulating housing is constructed of at least two separable pieces that allow access to the jacket when separated.

49. A gas chromatograph assembly comprising:
 means for injecting a sample;
 means for removing impurities from the injected sample;
 means for controlling the temperature of the impurity removing means including means for creating an air bath surrounding the means for removing impurities;
 insulating means surrounding the means for creating an air bath, wherein the insulating means is separate from the means for creating an air bath; and
 means for separating chemical components of the injected sample,
 wherein the impurities removing means is located upstream of the separating means.

50. The gas chromatograph assembly of claim 49, wherein the impurities removing means is replaceable.

51. The gas chromatograph assembly of claim 49, wherein the means for controlling the temperature of the impurity removing means includes means for heating the air bath.

* * * * *

UNITED STATES PATENT AND TRADEMARK OFFICE
CERTIFICATE OF CORRECTION

PATENT NO. : 7,520,920 B1
APPLICATION NO. : 11/367334
DATED : April 21, 2009
INVENTOR(S) : Gregory et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 231 days Delete the phrase "by 231" and insert -- by 302 days --

Signed and Sealed this

Fifteenth Day of September, 2009

David J. Kappos
*Director of the United States Patent and Trademark Office*